(12) United States Patent
Hobson et al.

(10) Patent No.: US 6,399,092 B1
(45) Date of Patent: Jun. 4, 2002

(54) ANHYDROUS, HYDROPHILIC ABSORBENT WOUND DRESSING (TUBE) WITH ANTIMICROBIALS OR OTHER PHARMACEUTICALLY ACTIVE AGENTS

(75) Inventors: David W. Hobson; David P. Jones; Pilar P. Duque, all of San Antonio, TX (US)

(73) Assignee: Healthpoint, Ltd., San Antonio, TX (US)

( * ) Notice: Subject to any disclaimer, the term of this patent is extended or adjusted under 35 U.S.C. 154(b) by 0 days.

(21) Appl. No.: 09/749,003

(22) Filed: Dec. 27, 2000

(51) Int. Cl.[7] .............................. A61K 9/70; A61K 9/14; A61L 15/00
(52) U.S. Cl. ..................... 424/443; 424/487; 424/445; 424/486
(58) Field of Search ................................. 424/443, 487, 424/445, 486

(56) References Cited

U.S. PATENT DOCUMENTS

| 4,226,232 A | 10/1980 | Spence ........................ 128/156 |
|---|---|---|
| 4,376,764 A | 3/1983 | Schmolka ..................... 424/78 |
| 4,563,184 A | 1/1986 | Korol .......................... 604/368 |
| 4,599,209 A | 7/1986 | Dautzenberg et al. ......... 264/7 |
| 4,803,066 A | 2/1989 | Edwards ...................... 424/132 |
| 4,920,158 A | 4/1990 | Murray et al. ............... 523/111 |
| 4,979,946 A | 12/1990 | Gilman ........................ 604/307 |
| 5,000,950 A | 3/1991 | Wuendisch ................... 424/78 |
| 5,013,769 A | 5/1991 | Murray et al. ............... 523/111 |
| 5,064,653 A | * 11/1991 | Sessions et al. ............. 424/445 |
| 5,631,301 A | 5/1997 | Osborne .................. 514/772.4 |
| 5,662,924 A | * 9/1997 | Rhodes ........................ 424/445 |
| 5,880,216 A | 3/1999 | Tanihara et al. ............... 525/61 |
| 5,885,237 A | 3/1999 | Kadash et al. ................. 602/48 |
| 5,968,001 A | 10/1999 | Freeman ....................... 602/42 |
| 6,039,940 A | 3/2000 | Perault et al. ........... 424/78.06 |
| 6,066,773 A | 5/2000 | Freeman ...................... 602/52 |

OTHER PUBLICATIONS

BASF Corporation Technical Bulletin, Pluronic® Block Copolymer NF Grade (Poloxamer NF Grades), 1992, NJ, pp. 1–11.

* cited by examiner

Primary Examiner—James M. Spear
Assistant Examiner—Blessing Fubara
(74) Attorney, Agent, or Firm—McKee, Voorhees & Sease, P.L.C.

(57) ABSTRACT

An anhydrous, hydrophilic wound dressing containing a superabsorbent polymer and an antimicrobial agent. Its anhydrous nature allows it, when applied to a wound site, to absorb wound fluid and slowly release its water-soluble active microbial agent into the wound.

19 Claims, 1 Drawing Sheet

ANHYDROUS, HYDROPHILIC ABSORBENT WOUND DRESSING (TUBE) WITH ANTIMICROBIALS OR OTHER PHARMACEUTICALLY ACTIVE AGENTS

FIELD OF THE INVENTION

This invention relates to wound dressings, particularly those which may be packaged in a dispensing tube.

BACKGROUND OF THE INVENTION

Draining wounds, such as Stage I–IV pressure ulcers, venous stasis ulcers, arterial ulcers, diabetic ulcers, donor sites, abrasions, lacerations, superficial burns, post-surgical wounds, and other external wounds, have often been a medical problem. Such wounds often contain necrotic tissue, and at the same time draining sites for blood, serum, etc. If such materials are allowed to accumulate and the wound not regularly cleaned, it is an ideal place for bacterial growth which, of course, promotes infection.

It has, of course, been recognized in the past that removal of necrotic tissue and wound exudate promotes faster healing, free from infection risk. In the past, others have attempted to formulate wound dressings containing water absorbent polymers such as starch superabsorbent polymers; however, such post compositions have met with limited commercial success.

One of the reasons believed to have been primary in this limited success is that all known past formulations have contained water. Water, when present in such formulations, reduces the viscosity, creates increased stability problems, and selectively holds water-soluble medicament actives so that they are not as easily released into wound exudate.

There is, therefore, a continuing need for improved formulations containing superabsorbent polymers which effectively allow the superabsorbent polymer to absorb wound exudate, while at the same time selectively releasing active medicaments into the wound on a gradual basis to allow the wound to be clean, dry and infection-free. This invention has as its primary objective the fulfillment of this need.

Another objective of the present invention is to provide an anhydrous, hydrophilic absorbent wound dressing which can effectively be contained in, and dispensed from a squeeze tube dispensing container, or be impregnated on a gauze pad.

Yet another objective of the present invention is to provide an anhydrous, hydrophilic absorbent wound dressing which contains active medicaments such as antimicrobials which, when applied to the wound site from a dispensing tube, allows wound fluid to be absorbed into the anhydrous, hydrophilic base, while simultaneously displacing into the wound the antimicrobial or pharmaceutically active ingredient.

A still further objective is to provide an anhydrous, hydrophilic absorbent wound dressing which allows slow release of the pharmaceutically active to the infection wound bed while simultaneously absorbing in a superabsorbent polymer, microbial-laden watery exudate.

The method and manner of accomplishing each of the above objectives will become apparent from the detailed description of the invention which follows hereinafter.

SUMMARY OF THE INVENTION

Figure 1:
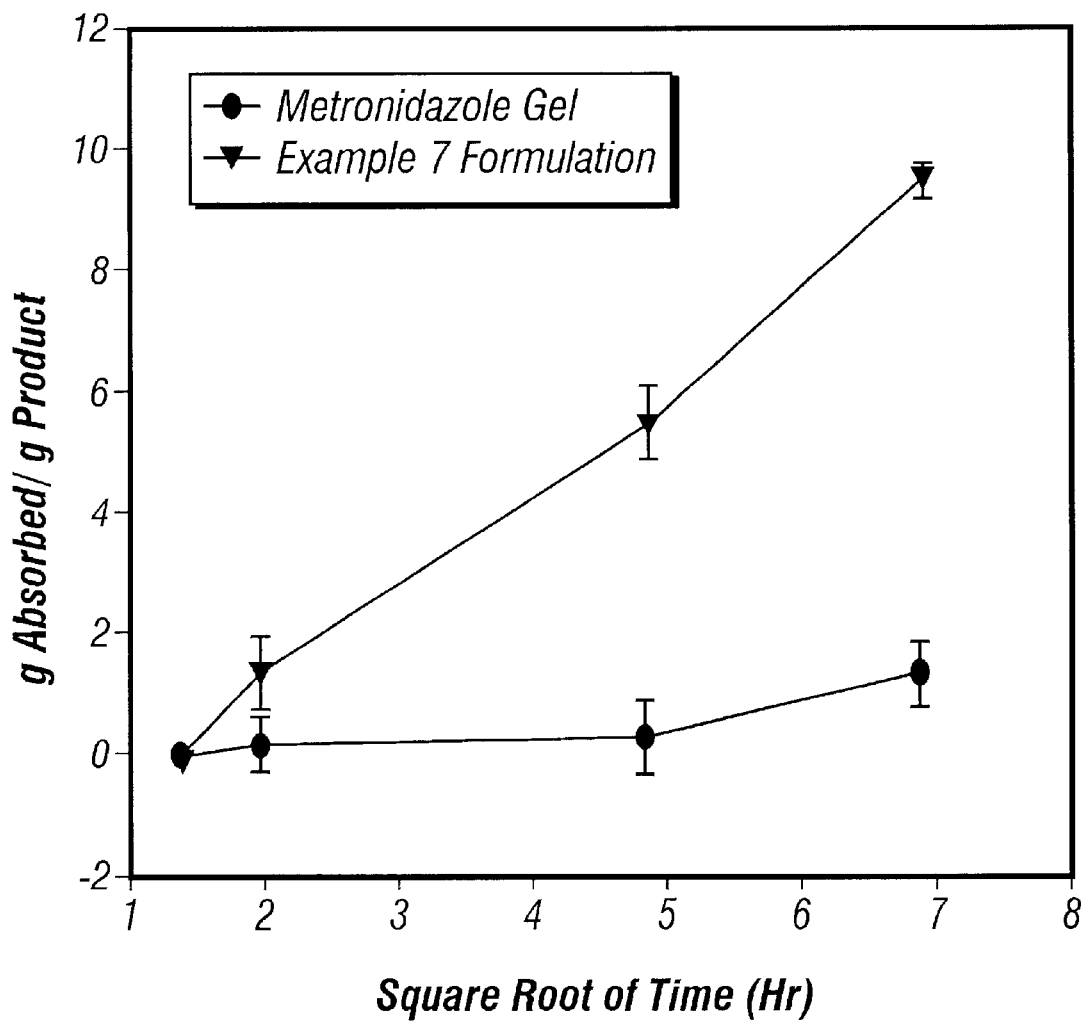
FIG. 1 shows in vitro absorbency of artificial wound fluid for the absorbent base of Example 7.

An anhydrous, hydrophilic superabsorbent wound dressing, having a viscosity capable of being contained in, and expelled from a dispensing tube or impregnated on a gauze pad is prepared. It is comprised of an anhydrous, hydrophilic gel-based carrier which is either a poloxamer or a polyethylene glycol, in combination with a superabsorbent polymer and an active medicament such as an antimicrobial agent. It functions to absorb microbial-laden exudate into the product, and simultaneously allows slow release of antimicrobial active medicament, for example, into the affected wound bed. These two events occur simultaneously because of the unique anhydrous nature of the formulation composition which allows this co-acting mechanism to occur.

DETAILED DESCRIPTION OF THE INVENTION

A unique co-action combination of the present invention allows simultaneous absorption of microbial-laden exudate from a wound while slowly releasing, for example, antimicrobial actives into the wound bed. The combination is of an anhydrous, hydrophilic gel base carrier which may be a poloxamer or polyethylene glycol with a superabsorbent polymer, which may be a starch polymer, a homopolymer, or a cellulose base superabsorbent polymer. The importance of the initial composition being anhydrous is that such is essential and critical to the consistent release of the effective concentration of the soluble active of the formulation as it interfaces with an open wound. Such is less likely to occur if the formulation initially contains water.

An anhydrous gel base carrier can be either a poloxamer gel base or a polyethylene glycol gel base. Both have been used in the past in the wound dressing environment, although in different types of formulations than those described herein.

Poloxamers are block copolymers commercially available from BASF Corporation under the registered trade name Pluronic® and Lutrol™ F. These are described as block copolymers of ethylene oxide and propylene oxide represented by the following chemical structure:

$\mathrm{HO\,(C_2H_4O)_x(C_3H_6O)_y(C_2H_4O)_xH}$

In the above formula x and y represent whole integers controlling the molecular weight and therefore the viscosity of the polymer. Generally x is from 2 to 150, and y is from 15 to 70. Preferably x is from 12 to 141, and y is from 20 to 56. As will be evident from the examples which follow, these poloxamers or pluronic polyols are available from BASF and are fully described in BASF available publications such as Technical Bulletin: Pluronic® Block Copolymer NF Grade (Poloxamer NF Grades), copyright 1992, available from BASF Corporation, 100 Cherry Hill Road, Parsippany, N.J. 07054. Disclosure of this Technical Bulletin is incorporated by reference.

Generally speaking, the polyoxyethylene portion of the polymer may vary from as little as 10 percent to as high as 85 percent. The higher the polyoxyethylene percentage, the more water-soluble becomes the total molecule or polymer. The substantially water-soluble polymers in the molecular weight range of between about 1000 and about 16,000 are preferable. These materials are readily available under the trade name Pluronic® or Lutrol™ F polyols. A preferred material of this class for use in the compositions of this invention is available under the trade name of Pluronic F68 and has an average molecular weight of about 8350, although it may vary in range between about 7680 and 9510. In this material "x" in the above formula can, for example, be 80 and "y" can be 27.

The other, or second general class of suitable gel material for the anhydrous, hydrophilic gel base carrier are generally polyols, and intended to be included within this term are polymeric ethers, polymeric aliphatic alcohols, either together or alone, and polyalkoxylated alcohols.

Polyols suitable for use in the present invention include dihydroxyalkanes such as glycols which have from 3 to 4 carbon atoms.

Polyhydroxyalkanes of the general formula $$C_nH_{(2n+2)}O_n$$

in which n is a number from 3 to 6 are suitable for the preparation of a dressing of the invention and are, for example, glycerin, sorbitol and mannitol.

A polyethylene glycol suitable as a polyol for the preparation of a dressing of the invention is a water-soluble one having a molecular weight in the range of from 200 to 8000. A polypropylene glycol that may be used is water-soluble and preferably has a molecular weight of in the range of from 400 to 4000. Such polymeric ethers and polyethylene glycols are sold by Union Carbide under the trademark Carbowax®, and generally are described in Technical Bulletin Carbowax® Polyethylene Glycols copyright 1981, which is incorporated herein by reference.

The amount of base, whichever one is chosen, can be from about 25% to about 99% by weight of the wound dressing, but is preferably within the range of from about 50% to 90%.

Turning next to the superabsorbent polymer, the ingredient can be a starch or non-starch superabsorbent polymer. For example, it can be a starch superabsorbent polymer or cellulose superabsorbent polymer, both with equally satisfactory results.

Graft copolymers of starch-polyacrylonitrile and non-starch homopolymers of polyacrylonitrile per se are known, as well as are methods for their preparation.

Thus, it is known that acrylonitrile can be grafted on starch using ceric salts as catalysts to form starch-acrylonitrile graft copolymers. See, for example, U.S. Pat. No. 2,922,768. Such graft copolymers can also be prepared by the reaction of acrylonitrile with preirradiated starch which is prepared by irradiation of starch with gamma rays or an electron beam. See Reyes, Clark, Comas, Russell, and Rise, Nuclear Applications 6, 509–517(1969). In such graft copolymers the starch serves as a backbone or building block on which the acrylonitrile is grafted, and therefore the starch need be present in only very small proportions with respect to the polyacrylonitrile moiety.

After the starch polyacrylonitrile graft copolymer is produced to make it valuable as a water-insoluble material having the ability to absorb large amounts of water, it is saponified. For example, U.S. Pat. No. 3,425,971 is directed to saponification of a graft copolymer in an aqueous potassium hydroxide solution.

As described in U.S. Pat. No. 4,558,100, a non-starch homopolymer is prepared by treating an aqueous mixture of acrylonitrile (or methacrylonitrile) and a polyfunctional monomeric cross-linking agent with a polymerization initiator to achieve polymerization and cross-linking of the acrylonitrile. The resultant cross-linked polyacrylonitrile is then saponified using an aqueous alcoholic solution of an alkali metal base, recovered by washing with an alcohol and filtering, and finally dried to obtain the solid granular superabsorbent. The non-starch homopolymer is classified as poly(2-propenamide-co-2-propenoic acid, sodium salt).

Suitable cross-linked cellulose derivatives include those of the hydroxy lower alkyl celluloses wherein the alkyl group aptly contains from 1 to 6 carbon atoms, e.g., hydroxyethylcellulose, hydroxypropylcellulose; and the carboxycelluloses e.g., carboxymethylhydroxyethylcellulose and carboxymethylcellulose.

Ionic cellulose derivatives such as the carboxy celluloses are suitable. Carboxymethylcellulose in the form of its sodium salt is a preferred cellulose derivative. It is readily available and is the cheapest form of carboxymethylcellulose. However, other salt forms may also be used, e.g., lithium and potassium.

Carboxymethylcellulose may be prepared according to conventional methods. Thus, it may be prepared by the reaction of cellulose with the sodium salt of chloroacetic acid in aqueous alkaline organic slurries. Thus, cellulose is steeped in sodium hydroxide solution, and the alkali cellulose is treated under controlled conditions with sodium monochloroacetate to form the sodium salt of carboxymethylcellulose and sodium chloride.

The carboxymethylcellulose may be cross-linked by forming chemical, e.g., ester or ether cross-linkages or thermal cross-linkages, depending on the mode of manufacture.

The most preferred superabsorbent polymers are those sold by Grain Processing Corporation, Muscatine, Iowa, under the trademark Water Lock® Superabsorbent Polymer. They are described in a grain processing Technical Bulletin, TB20-021296, with the preferred Water Lock polymer being from the WATER LOCK® G-400 series, which is a homopolymer material classed as a Poly (2-propenamide-co-2-propenoic acid, sodium salt). It is described in Product Data sheet 081297, which also is incorporated herein by reference. The most preferred Water-Lock is G-460. The particle size of the G-460 is smaller than the G-400 and provides for a smoother texture in the composition. The amount of the superabsorbent in the composition can vary, but will be within the general range of from 1% to 50% by weight of the total composition. Such levels have been found to give a desired absorbency rate. The preferred weight level is from 5% to 25%.

In addition to the above, the composition will, of course, contain an active medicament and may contsain structure-forming polymer ingredients. The structure-forming polymers could be present at a level of from 0% to 10%, and can include synthetic polymer materials such as polyvinylpyrrolidone or polyacrilamides. A suitable structure-forming polymer is a synthetic polymer known as Povidone. Another is Sepigel® from the Seppic Corporation. Such are used to aid in assuring a stable consistency.

The active medicament would generally be from about 0% to 20% by weight of the composition, and often it will be in combination with stabilizing preservatives such as Methylaparaben, Propylaparaben, Imide Urea or Benzyl Alcohol. For the most preferred compositions of the present invention, the active medicament will be water-soluble antimicrobial agents. Antifungal agents may be also employed, such as Miconazole Nitrate, Econazole Nitrate, and others. Likewise, antibiotics can be used such as Neomycin, Bacitracin, Polymixin, etc. The useful antimicrobials are not necessarily limited, and can be selected from the following list: Benzalkonium Chloride, Benzethonium Chloride, Benzoic Acid or salt form thereof, Benzoyl Peroxide, Benzyl Alcohol, Bispyrithione Salt, Borage Oil, Boric Acid, Cadexomer-Iodine, Camphorated Metacresol, Camphorated Phenol, Chlorhexidine Gluconate, Chlorobutanol, Cloflucarban, Dapsone, Dehydroacetic Acid or salt form thereof, Ethyl Alcohol, Eucalyptol, Extracts of Lavender Oil, Free fatty acids having from six to eighteen carbons, Glyceryl Laurate, Hexachlorophene, Hexitidine, Hexylresorcinol, Hydrogen Peroxide, Hydroxybenzoic Acids or salt forms thereof, Iodine Complexed with Phosphate Ester of Alkylaryloxy Polyethylene, Iodine Tincture, Iodine Topical Solution, Iodoquinol, Isopropyl Alcohol, Lipacide CG, Mafenide Acetate, Magnesium Pyrithione, Menthol, Merbromin, Mercufenol Chloride, Methyl Salicylate, Methylbenzethonium Chloride, Methylparaben, Metronidazole, Metronidazole derivatives, Nitrofurazone, Nonyl Phenoxypoly Ethanol-Iodine, n-Propanol, Organic Peroxides, p-chloro-m-xylenol, Phenol, Phenoxyethanol, Phenyl Alcohol, Poloxamer-iodine complex, Povidone Iodine, PVP-Iodine, Rose Hips Oil, Salicylic Acid, Secondary Amyltricresols, Selenium sulfide, Silver or salt form thereof, Silver Sulfadiazine, Sodium Oxychlorosene, Sodium Sulfacetmide, Sorbic Acid or salt form thereof, Sulfur, Tetrachlorosalicylanilide, Thymol, Tribromsalan, Triclocarbon, Triclosan, Undecoylium Chloride-iodine Complex, Zinc Pyrithione. In addition, antimicrobial peptides and proteins which have recently been developed could be employed.

The above list demonstrates, as illustrated by its length, that the topically active, or pharmaceutically active is non-limiting. Its only criteria are that it be compatible with the superabsorbent polymer, and the anhydrous, hydrophilic gel base carrier, and that it be water-soluble.

The compositions of the present anhydrous absorbent wound dressing are illustrated by the following examples. These examples should be taken as illustrative, and non-limiting.

| Ingredient | % w/w |
| --- | --- |
| Example 1 | |
| Poloxamer 124 | 61.5 |
| Poloxamer 338 | 17.0 |
| Acrylamide/Sodium Acrylate Copolymer (WaterLock G-460) | 20.0 |
| Povidone | 0.5 |
| Silver Sulfadiazine | 1.0 |
| Example 2 | |
| Poloxamer 124 | 60.0 |
| Poloxamer 338 | 11.0 |
| Acrylamide/Sodium Acrylate-Copolymer (WaterLock G460) | 20.0 |
| Povidone | 0.50 |
| Mafenide Acetate | 8.5 |
| Example 3 | |
| Poloxamer 124 | 57.2 |
| Poloxamer 338 | 21.7 |
| Povidone | 0.5 |
| Acrylamide/Sodium Acrylate Copolymer (WaterLock G460) | 20.0 |
| Chlorobutanol | 0.6 |
| Example 4 | |
| Polyethylene Glycol 400 | 64.25 |
| Polyethylene Glycol 3350 | 23.0 |
| Acrylamide/Sodium Acrylate Copolymer (WaterLock G-460) | 10.0 |
| Povidone | 2.00 |
| Metronidazole | 0.75 |
| Example 5 | |
| Polyethylene Glycol 400 | 59.42 |
| Polyethylene Glycol 3350 | 27.48 |
| Acrylamide/Sodium Acrylate Copolymer (WaterLock G-460) | 10.0 |
| Povidone | 0.85 |

| Ingredient | % w/w |
| --- | --- |
| -continued | |
| Gelatin | 2.0 |
| Methylaparaben | 0.25 |
| Example 6 | |
| Propylene Glycol | 84.4 |
| Sepigel ® 305 | 5.0 |
| Acrylamide/Sodium Acrylate Copolymer | 10.0 |
| Chlorobutanol | 0.6 |
| Example 7 | |
| Poloxamer 407 | 14.0 |
| Poloxamer 338 | 5.5 |
| Poloxamer 124 | 34.25 |
| Propylene Glycol | 25.5 |
| Acrylamide/Sodium Acrylate Copolymer (WaterLock G0460) | 20.0 |
| Metronidazole | 0.75 |

The formulations illustrated in 1–7 have been demonstrated as effective superabsorbent materials in the laboratory in in vitro fluid absorbent studies and in pharmaceutical ingredient stability studies. They also have been demonstrated as stable in dispensing squeeze tubes.

The results of in vitro fluid absorbency testing of the metronidazole-containing formulation provided by Example 7 are provided in FIG. 1 along with contrasting results for a commercially available metronidazole carbomer-based gel used in wounds. The wound fluid absorbency is significantly greater for the formulation provided in Example 7 relative to that for the commercial metronidazole gel. The artificial wound fluid used in the testing better simulates the characteristics of natural wound fluid than distilled water or physiological saline solutions and is formulated containing: 0.2% w/v fatty acids, 4.0% w/v albumin, 2.5% w/v globulins, 0.05% w/v triglycerides dissolved in phosphate buffered saline (pH 7.5).

What is claimed is:

1. An anhydrous, hydrophilic superabsorbent wound dressing of a viscosity capable of being contained in, and expelled from a dispensing tube, comprising:

an anhydrous, hydrophilic gel base carrier selected from the group consisting of poloxamers and polyols;

an effective amount of an antimicrobial agent; and a superabsorbent polymer.

2. The wound dressing of claim 1 wherein the poloxamers are block copolymers of ethylene oxide and propylene oxide of the structure:

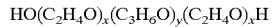

$$HO(C_2H_4O)_x(C_3H_6O)_y(C_2H_4O)_xH$$

wherein x is from 2 to 150 and y is from 15 to 70.

3. The wound dressing of claim 2 wherein x is from 12 to 141 and y is from 20 to 56.

4. The wound dressing of claim 1 wherein the polyol is a polyhydroxyalkane of the formula:

$$C_nH_{2n+2}O_n$$

wherein n is from 3 to 6.

5. The wound dressing of claim 1 wherein the superabsorbent polymer is selected from the group consisting of starch and non-starch super absorbent polymers.

6. The wound dressing of claim 5 wherein the superabsorbent polymer is a starch polymer.

7. The wound dressing of claim 5 wherein the superabsorbent polymer is a graft copolymer of starch polyacrylonitrile and non-starch homopolymers of polyacrylonitrile.

8. The wound dressing of claim 5 wherein the superabsorbent polymer is a poly(2-propenamide-co-2-propenoic acid sodium salt).

9. The wound dressing of claim 8 wherein the superabsorbent polymer is from 5% by weight to 25% by weight of the composition.

10. The wound dressing of claim 1 wherein the active medicament is selected from the group consisting of a water-soluble antimicrobial agent.

11. A method of treating wounds to simultaneously absorb microbial-laden wound exudate and to slowly release an antimicrobial agent into the wound, comprising:

applying to an external wound a treatment effective amount of a wound dressing, comprising:

an anhydrous, hydrophilic gel base carrier selected from the group consisting of poloxamers and polyols;

an effective amount of an antimicrobial agent, and a superabsorbent polymer.

12. The method of claim 11 wherein the poloxamers are copolymers of ethylene oxide and propylene oxide of the structure:

$$HO(C_2H_4O)_x(C_3H_6O)_y(C_2H_4O)_xH$$

wherein x is from 2 to 150 and y is from 15 to 70.

13. The method of claim 12 wherein x is from 12 to 141 and y is from 20 to 56.

14. The method of claim 11 wherein the polyol is a polyhydroxyalkane of the formula:

$$C_nH_{2n+2}O_n$$

wherein n is from 3 to 6.

15. The method of claim 11 wherein the superabsorbent polymer is selected from the group consisting of starch and non-starch super absorbent polymers.

16. The method of claim 15 wherein the superabsorbent polymer is a starch polymer.

17. The method of claim 15 wherein the superabsorbent polymer is a graft copolymer of starch polyacrylonitrile and non-starch homopolymers of polyacrylonitrile.

18. The method of claim 15 wherein the superabsorbent polymer is a poly(2-propenamide-co-2-propenoic acid sodium salt).

19. The method of claim 18 wherein the superabsorbent polymer is from 5% by weight to 25% by weight of the composition.

* * * * *